(12) United States Patent
Msika et al.

(10) Patent No.: US 8,722,023 B2
(45) Date of Patent: May 13, 2014

(54) DEPIGMENTING OR BRIGTHENING COSMETIC COMPOSITION COMPRISING AT LEAST ONE OXAZOLIN AS AN ACTIVE INGREDIENT

(75) Inventors: Philippe Msika, Versailles (FR); Nathalie Piccardi, Arceau (FR)

(73) Assignee: Laboratoires Expanscience, Courbevoie (FR)

( * ) Notice: Subject to any disclaimer, the term of this patent is extended or adjusted under 35 U.S.C. 154(b) by 1265 days.

(21) Appl. No.: 11/919,253

(22) PCT Filed: Apr. 27, 2006

(86) PCT No.: PCT/EP2006/061902
§ 371 (c)(1),
(2), (4) Date: Mar. 27, 2008

(87) PCT Pub. No.: WO2006/114443
PCT Pub. Date: Nov. 2, 2006

(65) Prior Publication Data
US 2009/0274637 A1 Nov. 5, 2009

(30) Foreign Application Priority Data
Apr. 27, 2005 (FR) ...................................... 05 04227

(51) Int. Cl.
*A61Q 19/00* (2006.01)
(52) U.S. Cl.
USPC ............................. 424/59; 424/400; 424/401

(58) Field of Classification Search
CPC ......... A61Q 1/00; A61Q 19/00; A61Q 19/08; A61Q 19/02
USPC ............................................................ 424/59
See application file for complete search history.

(56) References Cited

U.S. PATENT DOCUMENTS

| 4,876,249 A | 10/1989 | Rajadhyaksha | |
|---|---|---|---|
| 4,948,577 A * | 8/1990 | Hara | 424/59 |
| 5,686,489 A * | 11/1997 | Yu et al. | 514/557 |
| 2005/0075380 A1* | 4/2005 | Msika et al. | 514/374 |
| 2006/0122246 A1 | 6/2006 | Msika et al. | |

FOREIGN PATENT DOCUMENTS

| FR | 2 834 216 A | 7/2003 |
|---|---|---|
| FR | 2 856 294 A1 | 12/2004 |

OTHER PUBLICATIONS

R. Lusskin et al., "A New Reaction of Nitriles. V. Preparation of N-(2-Halo-1-ethyl)-amides," J. Amer. Chem. Soc., 72, (1950), pp. 5577-5578.

* cited by examiner

*Primary Examiner* — Abigail Fisher
*Assistant Examiner* — Luke Karpinski
(74) *Attorney, Agent, or Firm* — Birch, Stewart, Kolasch & Birch, LLP

(57) ABSTRACT

The invention relates to the cosmetic use of at least one oxazolin as a depigmenting active ingredient in a depigmenting composition, and to the associated cosmetic treatment method. The invention also relates to the use of at least one oxazolin for preparing an active medicament as a depigmenting agent, and to a depigmenting cosmetic composition comprising at least one oxazolin as a depigmenting active ingredient.

7 Claims, No Drawings

DEPIGMENTING OR BRIGTHENING COSMETIC COMPOSITION COMPRISING AT LEAST ONE OXAZOLIN AS AN ACTIVE INGREDIENT

The present invention relates to the use of a depigmenting or lightening cosmetic composition, comprising, as an active ingredient, at least one oxazoline.

The color of the skin is determined by several substances, namely vascular hemoglobin, dermal carotenoids and, most importantly, epidermal melanin. This melanin is produced by basal-layer melanocytes, under the action of tyrosinase, copper and oxygen.

Melanin in the skin is formed by a complex association of eumelanin and of pheomelanin.

Their biosyntheses are identical up to dopaquinone (double oxidation of tyrosine by tyrosinase, a cuproprotein enzyme), after which their paths diverge.

Brown eumelanin is an indole-5-6-quinone polymer whereas the compound pheomelanin, responsible for reddish-brown, contains nearly 10% sulfur and has the polymer structure of cysteinyldopa.

Enzymes other than tyrosinase take part in melanin genesis and control, namely dopachrome oxydoreductase, α-glutamyl transpeptidase, the glutathione system (reductase-peroxidase) and dopachrome tautomerase.

Under the effect of exogenous or endogenous stimulation, changes in skin can occur; such discolorations are referred as dyschromias (hyperchromias and hypochromias).

These changes can be based in the epidermis or dermis and can be due to variation in melanin quantity or melanocyte number.

Hyperchromia is the accumulation of melanic pigments or exogenous carotenoids or pigments.

Examples of hyperchromias include melasma, which is defined as an acquired facial hypermelanosis; melasma is observed in both sexes and all races. Melasma more often appears among women using an oral contraceptive and during pregnancy (mask of pregnancy, chloasma).

The mask of pregnancy, or chloasma, appears among women who have high levels of female hormones and whose skin is exposed to the sun. Thus, primarily pregnant females and those taking contraceptives are affected. Chloasma takes the form of brown pigmented blotches, often symmetrical, of more or less regular shape.

Aging of the skin is also characterized by the appearance of pigment spots. These include liver spots in the most frequently sun-exposed areas (face, hands, neck and shoulders), and senile lentigo, rather broad pigment spots, which appear on the hands, face and arms of the elderly.

Depigmenting or lightening agents are chemical compounds capable of acting at the tissue, cellular or subcellular level. They act on the formation, transport and color of melanin itself and on melanocyte viability (melanocytotoxicity).

In addition, it is necessary to detect and eliminate the factor inducing hyperpigmentation before treating it (UV, perfume, estrogen-progesterone) and to prescribe maximum-protection sun protection throughout aftercare.

Lastly, it is possible to eliminate the superficial layers of corneocytes containing melanin and thus achieve physical depigmentation of the surface, a treatment that also supports depigmenting-agent penetration.

A variety of motivations exist for lightening the skin. Lightening is sought in sub-Saharan Africa through the use of traditional or chemical solutions that are seriously harmful to skin appearance and structure. In the Far East, lightening is achieved with less-toxic molecules (arbutin, kojic acid, ascorbic acid).

A variety of molecules are used to treat hyperpigmentation spots on Caucasian subjects. The main one, hydroquinone, requires increased monitoring and is limited to 2% in cosmetics.

Thus, there is a need for compositions exhibiting depigmenting or lightening activity that are well tolerated by the skin.

This is why the present invention has as an object a dermatological and/or cosmetic composition, characterized such that it contains at least one oxazoline, as a depigmenting or lightening active ingredient.

In French patent application FR 2,834,216, the inventors disclosed the use of oxazolines in the inhibition of Langerhans' cell migration. This application thus discloses a medicament comprising at least one oxazoline as an active ingredient for the treatment or prevention of allergic and/or inflammatory and/or irritating reactions of the skin and/or mucous membranes.

In French application patent FR 2,856,294, the inventors disclose the use of oxazolines to inhibit lipogenesis in human adipocytes. This application thus discloses the use of a composition comprising at least one oxazoline, as an active ingredient, as a slimming composition and/or to prevent and/or treat cellulitis.

U.S. Pat. No. 4,876,249 discloses compositions comprising oxazolines in which the oxazolines promote the penetration of active physiological agents across the stratum corneum of the skin.

Surprisingly, the inventors now have demonstrated that oxazolines also exhibit depigmenting action. Thus, the inventors have developed a cosmetic and/or dermatological, depigmenting and/or lightening composition comprising at least one oxazoline as a depigmenting active ingredient.

The invention thus has as an object the use of at least one oxazoline, as a depigmenting active ingredient, in a depigmenting composition. The depigmenting composition is advantageously for reducing and/or eliminating and/or preventing pigmentation spots or to lighten naturally-pigmented skin.

The invention also has as an object a depigmenting cosmetic composition comprising at least one oxazoline as a depigmenting active ingredient.

The oxazolines according to the present invention are advantageously of the following general formula:

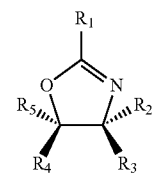

Type 1

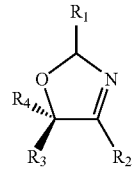

Type 2

Type 3

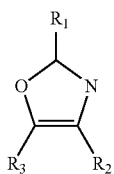

in which $R_1$ represents a linear or branched, saturated or unsaturated $C_1$-$C_{40}$ alkyl group optionally comprising one or more ethylene unsaturations as well as one or more substituents chosen from the group formed by hydroxy (OH) and $C_1$-$C_6$($OC_1$-$C_6$) alkoxy radicals; $R_2$, $R_3$, $R_4$ and $R_5$ represent, independent of each other, a hydrogen atom, a hydroxy radical or a linear or branched, saturated or unsaturated $C_1$-$C_{30}$ alkyl group, optionally comprising one or more ethylene unsaturations as well as one or more substituents chosen from the group formed by hydroxy (OH), $C_1$-$C_6$($OC_1$-$C_6$) alkoxy and $C_1$-$C_6$ alkoxy carbonyl ($COOC_1$-$C_6$) radicals. In the sense of the present invention, "$C_1$-$C_6$($OC_1$-$C_6$) alkoxy" means an alkoxy radical whose alkyl group has from one to six carbon atoms.

$R_1$ advantageously represents a linear or branched, saturated or unsaturated $C_8$-$C_{30}$ alkyl group, even more advantageously $C_8$-$C_{20}$, optionally comprising one or more ethylene unsaturations as well as one or more substituents chosen from the group formed by the hydroxy (OH) and $C_1$-$C_6$($OC_1$-$C_6$) alkoxy radicals.

Advantageously, $R_2$, $R_3$, $R_4$ and $R_5$ represent, independent of each other, a hydrogen atom, a hydroxy radical or a linear or branched, saturated or unsaturated $C_1$-$C_{10}$ alkyl group, even more advantageously $C_1$-$C_6$, optionally comprising one or more ethylene unsaturations as well as one or more substituents chosen from the group formed by hydroxy (OH), $C_1$-$C_6$($OC_1$-$C_6$) alkoxy and $C_1$-$C_6$ alkoxy carbonyl ($COOC_1$-$C_6$) radicals.

According to an advantageous embodiment of the present invention, said oxazoline is an oxazoline of type 1 chosen from the group comprised of 2-undecyl-4-hydroxymethyl-4-methyl-1,3-oxazoline; 2-undecyl-4,4-dimethyl-1,3-oxazoline; (E)-4,4-dimethyl-2-heptadec-8-enyl-1,3-oxazoline; 4-hydroxymethyl-4-methyl-2-heptadecyl-1,3-oxazoline; (E)-4-hydroxymethyl-4-methyl-2-heptadec-8-enyl-1,3-oxazoline; and 2-undecyl-4-ethyl-4-hydroxymethyl-1,3-oxazoline. Advantageously, said oxazoline is 2-undecyl-4,4-dimethyl-1,3-oxazoline, called OX100, of formula:

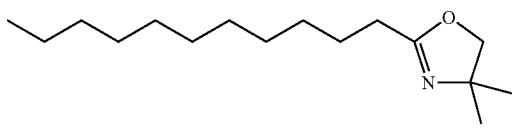 [SMILES: CCCCCCCCCCCC1=NC(C)(C)CO1]

Many synthesis routes are known for preparing the oxazolines according to the invention. Thus, said oxazolines can be prepared by chemical synthesis by the reaction of a fatty acid (or a methyl ester) and an amino-alcohol, most often in the presence of an azeotropic agent to help eliminate the water (and methanol) formed. Another possible synthesis route consists of condensing a halogen amide in the presence of a strong basis or sodium carbonate (R. M. Lusskin, J. Amer. Chem. Soc., 72, (1950), 5577). Oxazolines can also be synthesized by the reaction of epoxides with nitriles, by the reaction of thionyl chloride with hydroxyamides or by the action of acid on aziridinyl phosphine.

The oxazoline concentration in the inventive cosmetic and/or dermatological composition advantageously lies between roughly 0.01% and roughly 10% by weight, more advantageously between roughly 0.01% and roughly 5% by weight, even more advantageously between roughly 0.05% and roughly 3% by weight, compared to the total weight of the composition.

The inventive composition used can contain other depigmenting active ingredients, leading to a complementary or synergistic effect. The oxazolines can be combined with depigmenting agents known to a person skilled in the art such as hydroquinone and its derivatives, arbutin, retinoic acid, retinol, retinaldehyde, kojic acid, azelaic acid, vitamin B3 or PP, resorcinol and resveratrol derivatives, of licorice or white mulberry extracts, alpha lipoic acid, linoleic acid, cation chelators such as EDTA (ethylenediamine tetraacetic acid), and soy extracts.

Oxazolines can also be associated with antioxidants, leading to a complementary or synergistic effect. Specific examples of antioxidant agents include vitamin C, vitamin E, polyphenols (in particular those from green-tea, grape or pine extracts) and sulfur derivatives.

Oxazolines can also be combined with depigmenting agents such as Sepiwhite® (N-undecylenoyl-L-phenylalanine, Seppic), leading to a complementary or synergistic effect.

According to another aspect of the invention, the inventive cosmetic and/or dermatological compositions also contain, optionally with a synergistic effect, at least one UVB and UVA sun filter or screen; such mineral and/or organic screens or filters are known to those persons skilled in the art, who will adapt their selection and concentrations according to the degree of protection sought.

Lastly, the inventive cosmetic and/or dermatological compositions can also contain exfoliants such as the alpha-hydroxy and salicylic acids and ester derivatives, for example.

Lastly, the inventive cosmetic and/or dermatological compositions can also contain anti-inflammatory or soothing agents, cutaneous desensitizing agents such as NSAIDs (non-steroidal anti-inflammatories), dermocorticoids, PPAR (peroxisome proliferator-activated receptor) agonists, of derived from licorice, bisabolol, glycosylated or non-glycosylated isoflavones (from soya, for example), palmitoylethanolamide, unsaponifiables containing phytosterols and vitamin E, anti-COX and/or -LOX (inhibiting cyclooxygenase and/or lipoxidase), as well as thermal water, sea water or water reconstituted from exogenous trace elements.

According to an advantageous variant of the invention, the composition comprises as a depigmenting active ingredient an oxazoline with another depigmenting active ingredient such as Sepiwhite©. The composition advantageously comprises in addition a cocktail of vitamins (C and E) which provides anti-radical action and helps inhibit nitric oxide (NO).

Indeed, NO is implicated in the regulation of pigmentation.

The inventive dermatological and/or cosmetic composition comprises a dermatologically and/or cosmetically acceptable vehicle, i.e., a vehicle compatible with the skin. It can advantageously be provided in all of the galenical forms typically used for topical application, in particular in the form of an aqueous, hydro-alcohol or oil solution; an oil-in-water, water-in-oil or multiple emulsion; an aqueous or oil gel; an liquid paste or solid anhydrous product, a dispersion of oil in an aqueous phase using spherules (nanospheres, nanocapsules, lipid vesicles), a transdermal device or in any other form for topical application.

This composition can be more or less fluid and have the appearance of a white or colored cream, pomade, milk, lotion, serum, paste, foam or gel. Optionally, it can be applied to the skin in the form of an aerosol. It can also be provided in solid form, and, for example, in stick form. It can also be applied by means of a patch.

The inventive composition can also contain the typical additives used in the cosmetics field, such as stabilizers, preservatives, antioxidants, solvents, fragrances, chelators, odor absorbers, chemical or mineral filters, mineral pigments, surfactants, polymers, silicone oils and colorants.

The invention has also as an object a method of cosmetic treatment for reducing and/or eliminating pigmentation spots, characterized such that a composition comprising at least one oxazoline is applied by topical route. This cosmetic method of treatment makes it possible to standardize skin coloring. The composition is advantageously such as defined above.

Pigmentation spots include, without being limiting in any way, age spots, UV-induced spots, phototoxicity spots (perfume, medicament, exogenous toxin, burn) and chloasmas.

The invention also has as an object a method of cosmetic treatment for lightening the skin, characterized such that a composition comprising at least one oxazoline is applied by topical route. The composition is advantageously such as defined above.

The depigmenting properties of oxazolines can, according to another aspect of the invention, lead to the use of at least one oxazoline as an active ingredient for the preparation of an active medicament as a depigmenting agent.

The oxazoline used for the manufacture of the medicament is advantageously such as defined above. It can be used in association, optionally with a synergistic effect, at least one other depigmenting agent as defined previously and/or at least one organic or mineral sun filter and/or one anti-inflammatory agent.

The optimal modes of administration, dosing schedules and galenical forms of the inventive compounds and compositions can be determined according to the criteria generally taken into account in the establishment of a cosmetic and/or dermatological treatment adapted to, for example, a patient's type of skin.

The following examples illustrate the present invention.

EXAMPLE 1

Depigmenting Skin Cream No. 1

| INGREDIENTS | % w/w |
|---|---|
| Water | QSP 100 |
| Di-$C_{12-13}$ alkyl malate | 10.000 |
| Hydrogenated polydecene | 5.000 |
| Oryza sativa starch | 4.000 |
| Cetearyl alcohol | 3.200 |
| Glycerin | 3.000 |
| Hydrogenated coco-glycerides | 3.000 |
| Sorbitane stearate | 3.000 |
| Undecylenoyl phenylalanine | 2.000 |
| Ascorbyl glucoside | 2.000 |
| Tromethamine | 1.340 |
| Ceresine | 1.000 |
| Cetearyl glucoside | 0.800 |
| Fragrance | 0.500 |
| Gum xanthan | 0.400 |
| Potassium cetyl phosphate | 0.400 |
| Sclerotium gum | 0.300 |
| Sodium hydroxymethylglycinate | 0.200 |
| Oxazoline (OX 100) | 0.100 |
| Tocopherol | 0.100 |

EXAMPLE 2

Depigmenting Skin Cream No. 2

| INGREDIENTS | % w/w |
|---|---|
| Water | QSP 100 |
| Di-$C_{12-13}$ alkyl malate | 10.000 |
| Hydrogenated polydecene | 5.000 |
| Oryza sativa starch | 4.000 |
| Cetearyl alcohol | 3.200 |
| Glycerin | 3.000 |
| Hydrogenated coco-glycerides | 3.000 |
| Sorbitane stearate | 3.000 |
| Tromethamine | 1.340 |
| Ceresine | 1.000 |
| Cetearyl glucoside | 0.800 |
| Fragrance | 0.500 |
| Gum xanthan | 0.400 |
| Potassium cetyl phosphate | 0.400 |
| Sclerotium gum | 0.300 |
| Sodium hydroxymethylglycinate | 0.200 |
| Oxazoline (OX 100) | 0.200 |

EXAMPLE 3

Depigmenting Spray, SPF (Sun Protection Factor) 30

| Ingredients | % w/w |
|---|---|
| Water | QSP 100 |
| Pentaerythrityl tetraoctanoate | 15 to 30 |
| Titanium dioxide | 1 to 10 |
| Cyclomethicone | 1 to 10 |
| Zinc oxide | 1 to 10 |
| Methylene bis-benzotriazolyl tetramethylbutylphenol | 1 to 5 |
| ($C_{12}$-$C_{15}$)alkyl benzoate | 1 to 10 |
| 4,5,7-Trihydroxyisoflavone | 0.01 to 10 |
| Glycerin | 1 to 10 |
| Dicaprylyl ether | 1 to 10 |
| Cyclopentasiloxane | 1 to 10 |
| Ethylhexyl dimethicone ethoxy glucoside | 1 to 10 |
| Propylene glycol dioctanoate | 1 to 10 |
| Sodium chloride | 1 to 5 |
| PEG-45/dodecyl glycol co-polymer | 1 to 5 |
| PEG-30 dipolyhydroxystearate | 1 to 5 |
| Unsaponifiable soya oil | 1 to 5 |
| Dextrin palmitate | 1 to 5 |
| Oxazoline (OX 100) | 0.01 to 3 |
| Extract of Aloe barbadensis | 0.2 |
| Preservatives | QS |
| Zinc gluconate | 0.08 |

EXAMPLE 4

SPF 50 Depigmenting Cream

| Ingredients | % by weight |
| --- | --- |
| Water | QSP 100 |
| Pentaerythrityl tetraoctanoate | 15 to 30 |
| Titanium dioxide | 1 to 10 |
| Cyclomethicone | 1 to 10 |
| Zinc oxide | 1 to 10 |
| ($C_{12}$-$C_{15}$)alkyl benzoate | 1 to 10 |
| Undecylenoyl phenylalanine | 0.5 to 2 |
| Oxazoline (OX100) | 0.01 to 10 |
| 4,5,7-Trihydroxyisoflavone | 0.01 to 10 |
| Glycerin | 1 to 10 |
| Dicaprylyl ether | 1 to 10 |
| Cyclopentasiloxane | 1 to 10 |
| Ethylhexyl dimethicone ethoxy glucoside | 1 to 10 |
| Propylene glycol dioctanoate | 1 to 10 |
| Sodium chloride | 1 to 5 |
| PEG-45/dodecyl glycol co-polymer | 1 to 5 |
| PEG-30 dipolyhydroxystearate | 1 to 5 |
| Unsaponifiable soya oil | 1 to 5 |
| Dextrin palmitate | 1 to 5 |
| Preservatives | QS |
| Extract of *Aloe barbadensis* | 0.2 |
| Zinc gluconate | 0.08 |

EXAMPLE 5

Depigmenting Cream No. 3

| INGREDIENTS | % w/w |
| --- | --- |
| Water | QSP 100 |
| Di-$C_{12-13}$ alkyl malate | 10.000 |
| Hydrogenated polydecene | 5.000 |
| *Oryza sativa* starch | 4.000 |
| Cetearyl alcohol | 3.200 |
| Glycerin | 3.000 |
| Hydrogenated coco-glycerides | 3.000 |
| Sorbitane stearate | 3.000 |
| Ascorbyl glucoside | 2.000 |
| Tromethamine | 1.340 |
| Ceresine | 1.000 |
| Cetearyl glucoside | 0.800 |
| Fragrance | 0.500 |
| Gum xanthan | 0.400 |
| Potassium cetyl phosphate | 0.400 |
| Bisabolol | 0.300 |
| Sclerotium gum | 0.300 |
| Sodium hydroxymethylglycinate | 0.200 |
| Oxazoline (OX 100) | 0.100 |
| Tocopherol | 0.100 |

EXAMPLE 6

Evaluation of the Depigmenting Effect of OX100

Volunteers

The analysis of results relates to a panel of 21 adult female volunteers whose characteristics are presented in table 1 below.

TABLE 1 characteristics of the volunteer panel

| Age | Facial skin type | "Sensitive skin" | "Atopic" |
| --- | --- | --- | --- |
| 51 to 68 years (mean = 60) | dry = 57% mixed dry = 33% mixed oily = 10% | 24% | 19% |

Among these volunteers, 14% were North-African in origin and 86% Mediterranean, including 76% of phototype IV and 10% of phototype V. All of these volunteers had lentigo pigmentation spots on the hands and most had them on the face.

Results and Discussion

COLORIMETRIC MEASUREMENTS (Chromameter™): Variance homogeneity and distribution normality were verified in all cases.

In a Spot-Free Area

Measurements are taken on the hands, in an area without pigmentation spots. The results correspond to the means and deviations with respect to the mean-SEM. They are given in following tables 2 and 3.

Lightness Variable-L*

TABLE 2 lightness variable, before and after treatment, treated hand vs. control hand (spot-free area)

| HANDS | CONTROL | TREATED | Effect of the product (Student's t-test) |
| --- | --- | --- | --- |
| T = 0 | 58.5 ± 0.6 | 58.4 ± 0.7 | 0.810 |
| T = 6 weeks | 57.9 ± 0.6 | 59.2 ± 0.7 | 0.006 |
| Time effect (Student's t-test) | 0.173 | 0.080 | 0.017 |

Individual Typological Angle (ITA)

TABLE 3

Individual typological angle before and after treatment, treated hand vs. control hand (area without spots)

| HANDS | CONTROL | TREATED | Effect of the product (Student's t-test) |
| --- | --- | --- | --- |
| T = 0 | 39.0 ± 2.3 | 38.5 ± 2.4 | 0.818 |
| T = 6 weeks | 39.5 ± 2.8 | 44.1 ± 2.4 | 0.006 |
| Time effect (Student's t-test) | 0.760 | 0.000 | 0.008 |

The time and product effects results with values less than 0.05 are statistically significant. The result corresponding to both the time and product effects gives the value of the probability of the differences Δ (T=6 weeks minus T0) by the Student's t-test in a paired series (bilateral significance test, $p<0.05$).

A statistically significant increase in chromaticity coordinate L* of +2% (p=0.017), as well as in ITA of +13% (p=0.008), is observed for the hand treated with six weeks of applications, compared to the initial values and those obtained for the control hand.

In an Area with Spots (Measured for a Pre-Identified Pigmentation Spot)

Measurements are carried out on the hands in an area with pigmentation spots. The results correspond to the means and deviations with respect to the mean-SEM. They are given in following tables 4 and 5.

Lightness Variable-L*

TABLE 4 lightness variable, before and after treatment, treated hand vs. control hand (area with spots)

| HANDS | CONTROL | TREATED | Effect of the product (Student's t-test) |
|---|---|---|---|
| T = 0 | 52.3 ± 1.0 | 51.2 ± 1.1 | 0.218 |
| T = 6 weeks | 52.3 ± 0.9 | 52.4 ± 1.2 | 0.925 |
| Time effect (Student's t-test) | 0.986 | 0.022 | 0.048 |

The time and product effects results with values less than 0.05 are statistically significant. The result corresponding to both the time and product effects gives the value of the probability of the differences Δ (T=6 weeks minus T0) by the Student's t-test in a paired series (bilateral significance test, p<0.05).

Individual Typological Angle (ITA)

TABLE 5

Individual typological angle before and after treatment, treated hand vs. control hand (area without spots)

| HANDS | CONTROL | TREATED | Effect of the product (Student's t-test) |
|---|---|---|---|
| T = 0 | 10.4 ± 4.5 | 5.0 ± 4.5 | 0.150 |
| T = 6 weeks | 11.6 ± 4.1 | 11.0 ± 5.2 | 0.869 |
| Time effect (Student's t-test) | 0.606 | 0.020 | 0.078 |

The time and product effects results with values less than 0.05 are statistically significant. The result corresponding to both the time and product effects gives the value of the probability of the differences Δ (T=6 weeks minus T0) by the Student's t-test in a paired series (bilateral significance test, p<0.05).

A statistically significant increase in chromaticity coordinate L* of +2% (p=0.048 is observed for the hand treated with six weeks of applications, compared to the initial values and those obtained for the control hand.

Clinical Evaluation

Hands

The results of the statistically significant variation, after six weeks of application, of some of the criteria evaluated are given in table 6 below:

TABLE 6

Variation of the skin of the hand, after treatment

| | TREATED |
|---|---|
| SKIN UNIFORMITY | +10% (p = 0.0209) |
| SKIN LIGHTNESS | +16% (p = 0.0002) |
| INTENSITY OF THE PIGMENTATION SPOT | −5% (p = 0.0143) |

The percentages correspond to variations with respect to the initial evaluations, the p value corresponds to probability p with respect to the initial evaluations (Wilcoxon test, bilateral significance test, p<0.05). For measurements of pigmentation spot intensity, the intensity of the spot is identified beforehand.

Face

The results of the statistically significant variation, after six weeks of application, of some of the criteria evaluated are given in table 7 below:

TABLE 7

Variation of the skin of the hand, after treatment

| | TREATED |
|---|---|
| COLOR UNIFORMITY | +4% (p = 0.0455) |
| COLOR LIGHTNESS | +22% (p = 0.0001) |
| INTENSITY OF THE PIGMENTATION SPOT | −8% (p = 0.0196) |

The percentages correspond to variations with respect to the initial evaluations, the p value corresponds to probability p with respect to the initial evaluations (Wilcoxon test, bilateral significance test, p<0.05). For measurements of pigmentation spot intensity, the intensity of the spot is identified beforehand.

Overall Assessment of the Product's Acceptability and Effectiveness by the Volunteers Fifty-seven percent of the volunteers reported the product to have good to very good acceptability and 29% of the volunteers reported the product to have somewhat good acceptability.

Thirty-eight percent of the volunteers reported the product to have somewhat good to good effectiveness as a depigmenting/lightening product.

Assessment of Cutaneous Acceptability by the Volunteers

Ninety-five percent of the volunteers reported no cutaneous manifestations and 100% of the volunteers reported no ocular manifestations.

Consequently, OX100 is an effective, dermatologically well-tolerated depigmenting active ingredient.

EXAMPLE 7

Evaluation of the Depigmenting Effect of an Inventive Composition

The cosmetic depigmenting effectiveness and clinical cutaneous compatibility of the inventive cosmetic formula was studied within the framework of facial melasma.

Products:

Depigmenting Dream: Composition of Example 1

The product is used morning and evening on brown spots, after washing, on dry skin. The skin of the subjects tested is protected from solar radiation by the application of a SPF 60 total screen.

During the study, no other depigmenting product (cosmetic or local medicament) is applied locally to the areas concerned.

I-Investigation Methods
- self-estimate using a visual analog scale, for 60 days, under dermatological monitoring, and
- open biometeorological study with measurements of the melanic index using a Mexameter, standard photographs and UV photographs.

These evaluations and measurements were performed before the product was used and then after 60 days.

This study shows the cosmetic depigmenting effectiveness of the depigmenting cosmetic formula of example 1, by comparing the progress of the various components of melasma.

This formula was used within the framework of melasma-type acquired hyperchromias in order to contribute to the improvement of cutaneous state, in particular with regard to the effect on the reduction of color intensity in the hyperpigmented areas.

The good cosmetic acceptability and allergological tolerance of the formula were studied in parallel.

Principal Characteristics of the Panel

The 20 female volunteers participating in the study, ranging between 20 and 61 years (mean=42.7), were divided into 10-year age groups:

| Complexion: | average | 5 subjects |
| --- | --- | --- |
| | mate | 14 subjects |
| | African | 1 subject |
| Type of skin: | normal-to-dry | 5 subjects |
| | dehydrated senescent | 2 subjects |
| | dry | 1 subject |
| | oily, mixed | 3 subjects |
| | mixed | 8 subjects |
| | oily | 1 subject |
| Cutaneous reactivity: | increased | 3 subjects |
| | increased + erythrosis | 1 subject |
| | normal | 16 subjects |
| Phototype: | IV | 5 subjects |
| | V | 14 subjects |
| | African | 1 subject |

In this study, only hyperpigmented melasma lesions of the face having developed for more than six months and less than 10 years were selected. The hormonal origin of the melasma lesions is clear in nine of the subjects; it is probable in 10 subjects; for one subject an inflammatory origin is probable.

Clinical Study

At the beginning of treatment (D0), and then after 60 days of treatment (D60), clinical state was evaluated using MASI (melasma area and severity index) scoring, as described by Kimbrough-Green et al., Arch Dermatol 1994; 130:727-733.

The calculation used was that of the simplified MASI, i.e.:

$$(m\,MASI)=(D+H)*A \quad (Eq\,1)$$

Biometeorological Measurements

The melanic index of the skin was measured using a Mexameter, the diameter of the surface to measure being 5 mm.

The melanic index (MI) was calculated according to the following equation:

$$MI=(500/\log 5)*(\log(\text{infrared reflection/red reflection})+\log 5) \quad (Eq\,2)$$

The melanic index was measured on the right and left test areas before any product is used and then after 60 days.

Measurement areas: two hyperpigmented areas and two healthy areas on each side, the hyperpigmented areas receiving the product, and an area of healthy skin in the periphery of each hyperpigmented area.

Standard and UV Photographs

Standard photographs, right profile and left profile, were taken at both study time points.

UV photographs, right profile and left profile, were taken at both study time points and were computer processed to reveal color distribution. They were used to precisely identify the hyperpigmented areas.

Tolerance

An evaluation of overall tolerance was carried out at D60 according to a four-level severity scale.

Overall Assessment of Effectiveness

At D60, the depigmenting effectiveness of the product was determined using the following scale: not at all satisfactory, fairly satisfactory, satisfactory, very satisfactory.

Self Estimate

At D60, subjects were given a questionnaire concerning the cosmetic qualities of the product tested. A subjective psycho-sensory assessment of the cosmetic acceptability of the product and its conditions of use was carried out using a questionnaire given to each volunteer at D60.

II) Analysis of Results (60th Day=T1):

A) Clinical Study Using MASI Scoring

Cutaneous state was monitored, starting with the initial state noted at the beginning of the study, by the dermatologist after 60 days of use of the product tested.

Initially, the mean MASI score for all of the volunteers analyzed is 20.8. After 60 days of use, mean MASI score is 13.3.

MASI statistical analysis: a Wilcoxon equality test for matched samples was carried out to determine if the means observed between each study time point were statistically different.

Thus, a statistically significant difference ($p=0.0006$) is observed, with a reduction in clinical MASI score of 36.06% at the 60th day of use.

Overall hyperpigmentation reduction was evaluated by the dermatologist after 60 days according to various clinical criteria.

After 60 days, the dermatologist judged that hyperpigmentation was reduced in a "satisfactory" or "very satisfactory" way in 42.1% of cases.

B) Changes in the Melanic Index

For each side treated, the melanic index was measured for symmetrical or similar areas exhibiting hyperpigmentation in order to study the depigmenting effect of each product. Moreover, the melanic index was measured on a normally-pigmented area of healthy skin in order to have a base reference.

The results of the measurements taken at each study time point on each subject were averaged by area (treated areas, areas of healthy skin).

At D0 the melanic indices measured for the hyperpigmented areas and for the healthy skin are different statistically ($p<0.0001$) and the difference between the two measurements is 20.29 (arbitrary units).

The mean results observed for the healthy control skin are as follows:
- at T0 the mean value of the melanic index is 500.89,
- at T1 the mean value of the melanic index is 500.08.

By comparing the value of the melanic index in healthy skin between T0 and T1 a significant difference is not observed ($p=0.6149$).

The mean results observed for the hyperpigmented treated areas are as follows:
- at T0 the mean value of the melanic index is 521.18,
- at T1 the mean value of the melanic index is 513.92.

Between T0 and T1 a significant difference ($p=0.0066$) is observed between the value of the melanic index measured for the hyperpigmented areas: the difference between the measurement at T0 and the measurement at T1 is 7.26 (arbitrary units) and the value of the melanic index is decreased by 1.39%.

On the other hand, at T1 there remains a significant difference (p=0.0003) between the melanic indices measured for the hyperpigmented areas and for the healthy skin. The difference between measurements at T1 was 13.84 (arbitrary units), whereas it was 20.29 at T0.

C) Tolerance

The study of functional signs on each side of the face, namely feelings of tugging, tingling or burns, does not show any significant variation.

D) Volunteer Self-Estimates:

Between T0 and T1 (60 days), there is a statistically significant difference for the following self-estimated signs (Wilcoxon test):

| | |
|---|---|
| Brown spot color intensity, which decreases by | 28.1% |
| The skin is lighter, with an increase of | 63.1% |
| Color is lighter, with an increase of | 90.7% |
| Color is more uniform, with an increase of | 73.9% |
| Color is more transparent, with an increase of | 83.4% |

Consequently, an inventive depigmenting cosmetic composition, comprising OX100 as a depigmenting active ingredient, is effective and well accepted dermatologically for melasma-type hyperpigmented lesions.

EXAMPLE 8

Effects of OX100 on Cutaneous Pigmentation

The effect of OX100 was studied on the production of melanin by normal human melanocytes in co-culture (NHEM-NHEK; M/K) irradiated or not.

Test Principle and Protocol:

Principle:

Melanocyte/keratinocyte co-cultures (NHEM-NHEK; M/K) are incubated for 240 hours, in the absence or presence of OX100. The quantity of melanin present in the cells after incubation is measured by spectrophotometry.

Protocol:

1) M/K co-cultures are inoculated in medium free of PMA (phorbol myristate acetate) and are brought to 60-80% confluence for the test.

2) Three identical culture series are prepared in order to measure:
cytotoxicity by a MTT (tetrazolium salt) test and by morphological observation of the cells,
quantity of melanin,
quantity of total proteins (in order to determine the ratio of melanin to total protein).

3) Treatment conditions are as follows:
OX100 at three concentrations: $2\times10^{-6}$, $10^{-5}$, $2\times10^{-5}$ M.
Kojic acid (reference depigmenting molecule).
IBMX (3-isobutyl-1-methylxanthine, pro-pigmenting reference molecule).

Each treatment condition is carried out in triplicate. The co-cultures are incubated for 240 hours in the presence or absence of the compounds above.

Irradiation by ultraviolet rays (25 mJ/cm$^2$ of UVB+300 mJ/cm$^2$ of UVA) is carried out four times per day for consecutive four days.

At the end of the treatment, the cellular monolayers are washed. After cell lysis, the melanin crystals are extracted and solubilized. The melanin is quantified by measurement of the OD (optical density) at 450 nm and by comparison with a range of melanin standards.

Results:

Study of Viability:

OX100 is not toxic for the M/K co-cultures at the three concentrations tested (same remark for the reference molecules), the results are given in following table 8.

TABLE 8

Viability percentage (MTT test)

| Treatment | Concentration | Without UV | With UV |
|---|---|---|---|
| Control | — | 100 | 100 |
| Kojic acid | 0.0156 mg/ml | 102 | 99 |
| IBMX | 200 µM | 118 | 111 |
| OX100 | $2 \times 10^{-5}$ M | 115 | 105 |
| | $10^{-5}$ M | 108 | 99 |
| | $2 \times 10^{-6}$ M | 102 | 97 |

Study of Effectiveness:

The effect of the product on melanin production was evaluated in the M/K co-cultures with and without irradiation (table 9).

TABLE 9

Percentage in variation of the quantity of melanin compared to the control

| Treatment | Concentration | Without UV | With UV |
|---|---|---|---|
| Control | — | 100 | 100 |
| IBMX | 200 µM | 118* (+15%) | 114* (+14%) |
| Kojic acid | 15.6 µg/ml | 74* (−35%) | 83* (−20%) |
| OX100 | $2 \times 10^{-5}$ M | 89* (−12%) | 104 (+4%) |
| | $10^{-5}$ M | 104 (+4%) | 99 (−1%) |
| | $2 \times 10^{-6}$ M | 102 (−1%) | 100 (0%) |

*results statistically different from the control (p < 0.01, Dunnett's test)

OX100 significantly decreases (p<0.01) the synthesis of melanin in non-irradiated co-cultures, roughly 12% of inhibition at $2.10^{-5}$ M.

OX100 can thus have a lightening effect on normal skin.

On the irradiated study model, OX100 neutralizes the effect of ultraviolet rays. Indeed, no significant difference is observed between the control and the treatments by the product of the test. There is no increase in melanin under UV and the skin has the same color as the non-irradiated control.

Conclusion

OX100 can be of interest dermo-cosmetically as a depigmenting product, for the treatment of cutaneous hyperpigmentation, by its capacity to neutralize the melanin overproduction induced by ultraviolet rays, and also by inhibiting melanin's synthesis under non-irradiating conditions.

The invention claimed is:

1. A method of cosmetic treatment for depigmenting the skin by acting on the melanin or the melanocyte, said method comprising
selecting as a person in need of such depigmentation a person having lentigo pigmentation spots and/or hyperpigmented melasma lesions on his or her skin, and then administering a composition comprising at least one oxazoline selected from the group consisting of 2-undecyl-4-hydroxymethyl-4-methyl-1,3-oxazoline; 2-undecyl-4,4-dimethyl-1,3-oxazoline; (E)-4,4-dimethyl-2-heptadec-8-enyl-1,3-oxazoline; 4-hydroxymethyl-4- methyl-2-heptadecyl-1,3-oxazoline; (E)-4-hydroxymethyl-4-methyl-2-heptadec-8-enyl-1,3-oxazoline, and 2-undecyl-4-ethyl-4-hydroxymethyl-1,3-oxazoline, as a depigmenting active ingredient, to said person in need thereof, thereby depigmenting said lentigo pigmented spots and/or hyperpigmented melasma lesions.

2. The method of cosmetic treatment for depigmenting the skin according to claim 1, wherein the person in need of such depigmentation is selected among women using an oral contraceptive or during pregnancy and is a person having hyperpigmented melasma lesion on her skin.

3. The method of cosmetic treatment for depigmenting the skin according to claim 1, wherein said composition is applied by a topical route to said person in need thereof.

4. The method of cosmetic treatment for depigmenting the skin according to claim 1, wherein said oxazoline is the 2-undecyl-4,4-dimethyl-1,3-oxazoline of formula:

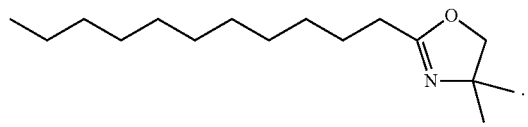 [SMILES: CCCCCCCCCCCC1=NC(C)(C)CO1]

5. The method of cosmetic treatment for depigmenting the skin according to claim 1, wherein said composition comprises between 0.01% and 10% by weight of the oxazoline compared to the total weight of the composition and a cosmetically acceptable medium.

6. The method of cosmetic treatment for depigmenting the skin according to claim 1, wherein said composition also comprises another depigmenting active ingredient.

7. The method of cosmetic treatment for depigmenting the skin according to claim 1, wherein said composition comprises in addition at least one organic or mineral sun filter.

\* \* \* \* \*